United States Patent [19]

Saunders

[11] Patent Number: 4,855,931

[45] Date of Patent: Aug. 8, 1989

[54] STOCHASTIC METHOD FOR FINDING MOLECULAR CONFORMATIONS

[75] Inventor: Martin Saunders, Guilford, Conn.

[73] Assignee: Yale University, New Haven, Conn.

[21] Appl. No.: 173,397

[22] Filed: Mar. 25, 1988

[51] Int. Cl.[4] .................. G06F 15/46; G01N 33/00
[52] U.S. Cl. .................................. 364/499; 434/278; 436/8; 436/183
[58] Field of Search .................. 364/496, 497, 499; 434/278, 279, 280, 281, 283; 436/8, 182, 183

[56] References Cited

U.S. PATENT DOCUMENTS 4,701,838 10/1987 Swinkels et al. .................. 364/498
4,704,692 11/1987 Ladner .................................. 364/496

OTHER PUBLICATIONS

Wiberg et al, "Application of Strain Energy Minimization to the Dynamics of Conformational Changes", *Journal of Amer. Chem Soc.*, 94:24, Nov. 29, 1972, pp. 8426-8430.

*Primary Examiner*—Parshotam S. Lall
*Assistant Examiner*—Brian M. Mattson
*Attorney, Agent, or Firm*—Perman & Green

[57] ABSTRACT

This is a stochastic method for determing the likely conformations of a molecule by starting with an initial molecular structure along with given atomic coordinate positions and defined bonds between atoms. Each of the atom's initial X, Y and Z coordinates are modified by the combination therewith of random numbers to create a new random coordinate position for each atom. A predetermined constraint is placed on the distance of each new coordinate from each initial coordinate. The steric energy of the reconfigured molecule is then calculated, stored and a new set of randon numbers combined with the atomic coordinates and the steric energy of the new structure calculated. The process is repeated until most, if not all, steric minima are detected and the structures associated therewith are determined.

9 Claims, 7 Drawing Sheets

FIG. 1

$E_s = \frac{K_r}{2}(r-r_0)^2$

FIG. 2

$E_\Theta = \frac{K_\Theta}{2}(\Theta-\Theta_0)^2$

FIG. 3

$E_t = K_w(1-\cos 3w)$

INITIALIZATION PROCESS

FIG. 6

FIG. 7    "KICK" PROCESS

CYCLOHEPTONE
"CHAIR CONFORMATION"

FIG. 10

CYCLOHEPTONE
"KICKED"

FIG. 11

CYCLOHEPTONE
"BOAT CONFORMATION"

STOCHASTIC METHOD FOR FINDING MOLECULAR CONFORMATIONS

FIELD OF INVENTION

This invention relates to molecular mechanics and more particularly to a method for determining the likely conformations of a molecule by the location of steric energy minima.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

Molecular mechanics is the name given to a widely used calculational method for providing accurate structures and energies for molecules. It has been long known that by employing the fundamentals of quantum mechanics, very accurate models of molecular structure could be achieved. Unfortunately, once the model size exceeded 15 or 20 atoms, the calculation became so time consuming as to be practically unsolvable. To overcome this problem, various models for the interaction of groups of atoms in molecules have been derived which provide reasonable approximations of interatomic relationships and energy distributions. A text which describes the field of molecular mechanics is entitled, appropriately, "Molecular Mechanics" by Burkert and Allinger, ACS Monograph 177, American Chemical Society, Washington, D.C. 1982.

The ability to calculate the structure and energies of a molecule are important for several reasons. As is well-known to chemists, the shape of a molecule is directly related to its properties. For instance, biologically active molecules are effective because they fit into certain openings in proteins. If it is desired to interfere with a natural action, a molecule must be designed which fits into that same opening and acts to inhibit the molecules action. This gives rise to the need to know the detailed structure for molecules, their bond distances, angles, etc.

While there are a number of methods for experimentally determining molecular structures, (e.g., X-Ray crystallography,) they first require the availability or synthesis of the substance, then the growing of a suitable crystal, then the accumulation of the X-Ray data and finally, computer processing of the data to obtain the structure. This process is time consuming and expensive at best, and difficulties at any step many times make it impossible.

Molecular Mechanics requires that the internal force fields in the molecule be approximated. For the purposes of the model, each atom is normally represented as a point and is connected to other atoms by bonds equivalent to springs. If a bond between two atoms (diatomic) is either stretched or compressed from an equilibrium distance, the bond is considered to increase in potential energy. Forces which act along covalent bonds and attempt to restore the equilibrium bond length are a component of the "valence force field".

In the case of a triatomic molecular model, (includes three atoms and has two bonds), the angle between the bonds is known as the bond angle and may also be stressed from its equilibrium point by the molecular structure. Both the diatomic and triatomic models naturally have all atoms in a single plane. However, when a fourth atom is introduced, there can be a torsion or dihedral angle between two planes, each one containing three of the atoms. Additionally, there are forces extant between atoms which are not directly bonded, which forces also come into play in the consideration of molecular structures.

It is the sum of all four of these potential energies, i.e., stretching energy, bending angle energy, torsion angle energy and non-bonded energy which comprise the steric energy of a molecule. Each of these individual energies will be described in further detail hereinbelow. Suffice it to say at this juncture that the basic idea is that bonds in a molecule have "natural" lengths and inter-bond angles, and molecules adjust their geometry so as to accommodate these values in most simple cases. In more strained systems, the molecules deform in predictable ways with strain energies that can be accurately calculated. It is clear, however, that there are certain preferred molecular structures which exhibit minimal steric energies and are most stable and most likely to exist. From a definitional point of view, an energy minimum in a molecule is referred to as a "conformer" or a "conformation". Butane, for instance, has three conformers which correspond to three energy minima. With more complicated molecules, there will, in general, be a large number of energy minima of different steric energies.

As aforestated, the molecular mechanics model of two atoms joined by a valence bond may be thought of as two points joined by a spring which has a natural value and which may be either compressed or extended. The angle of joinder between bonds in a triatomic species is similar in function to the bond "spring" in that it has a natural or unstressed angle and may be stressed to either compact or expand depending upon the molecular structure. The energy models of these atomic inter-relationships are shown in the upper right hand corners of FIGS. 1 and 2 respectively.

Figure 1:
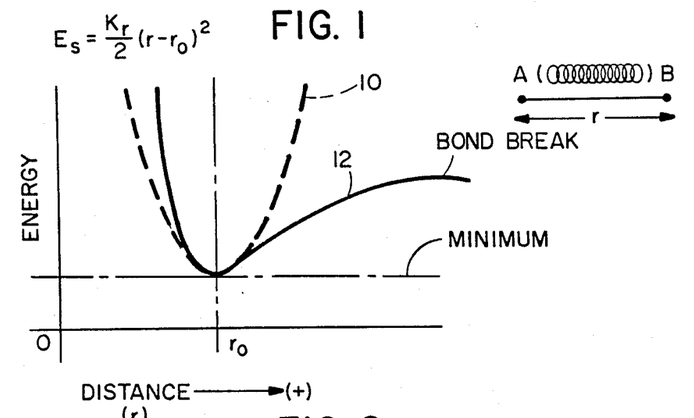
FIG. 1 illustrates the relationship between energy and bond distance between atoms.

In FIG. 1, the bond stretching energy function is shown as follows:

$$E_s = k_r(r - r_0)^2$$

where
  $r$ = actual bond distance
  $r_0$ = nonstressed bond distance
  $k_r$ = stretching force constant The function $E_s$ (i.e., the variation of bond energy with bond distance) is charted by dotted line 10 in FIG. 1. The actual variation of bond energy with bond stretching is shown by curve 12 which varies from the model by indicating that if the bond distance expands too far, the bond breaks and there is no further change in energy. Since that is not of practical concern, the model serves well to define the relationship. It is also to be noted that at distance $r_0$, the energy is at a minimum. Thus, $r_0$ is defined as the equilibrium bond distance.

Figure 2:
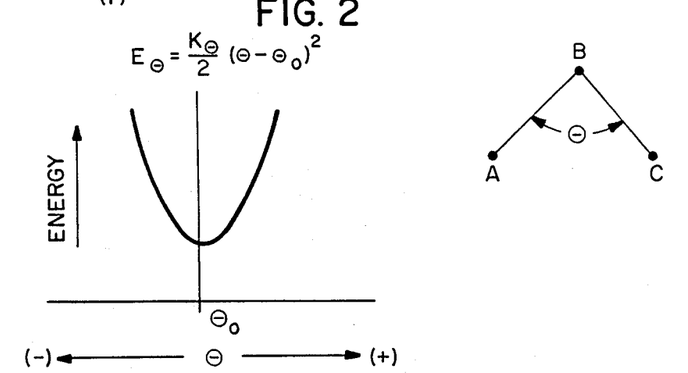
FIG. 2 is a plot of energy versus bend angle in a triatomic molecular structure.

Turning to FIG. 2, a similar function is shown for angle bending as follows:

$$E_\theta = \frac{k_\theta}{2}(\theta - \theta_0)^2$$

where $\theta$ = actual angle between bonds
$\theta_o$ = nonstressed bond angle
$k_\theta$ = angle bending force constant It will be noted that the function which defines $E_\theta$ describes a parabola which has a minimum at $\theta_o$ (the equilibrium angle).

Figure 3:
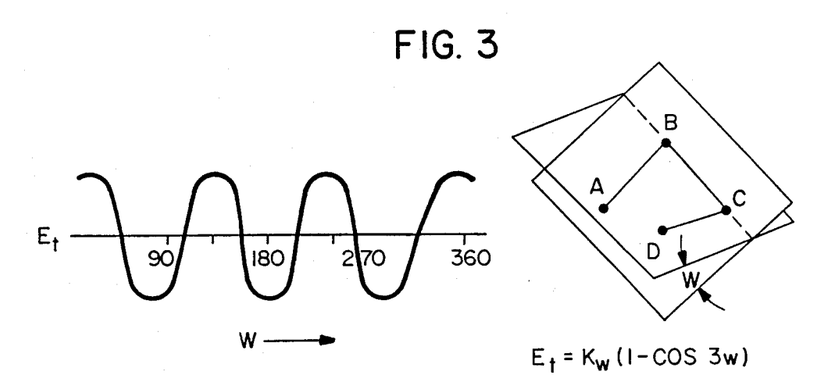
FIG. 3 is a plot of the variation of energy with torsion angle in a quadratomic molecule.

With four or more atoms, one of the atoms (in this instance atom D in FIG. 3) may be out of the plane of the other three atoms A, B and C. In such a case, there is a torsion or dihedral force exerted on the molecular structure. The energy function which expresses the torsional relationship is a cosine function which is expressed as follows:

$$E_t = k_w(1 - \cos(3w))$$

where
w = torsion angle
$k_w$ = torsional constant

The chart in FIG. 3 shows a plot of the torsion energy function $E_t$ as torsion angle $\theta$ varies from 0° to 360°.

Figure 4:
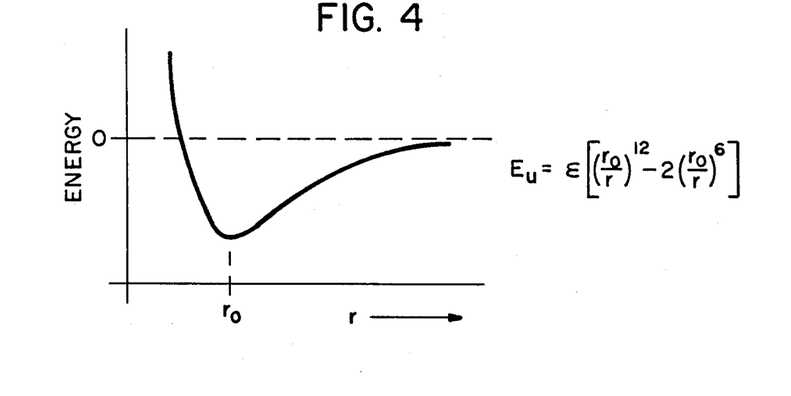
FIG. 4 is a plot of the variation of energy with interatomic distance for non-bonded atoms.

The last energy function employed in conventional mechanics is that which results from non-bonded interactions between atoms, (i.e., as shown in FIG. 3, it is the interaction between atoms A and D). As aforestated, all of these functions are models of the actual relationships and, at best, are approximations. This is more so with respect to non-bonded interactions than with the other energy equations. The function shown in FIG. 4 for non-bonded energy is just one of a number which may be used. In the equation shown in FIG. 4, epsilon defines the depth of the potential well, $r_o$ the minimum energy distance between the two atoms and r the actual distance between the two atoms. A plot of the equation of FIG. 4 is shown to the left of the equation.

The constants for each of the equations shown in FIGS. 1-4 may be experimentally determined, and some are shown in the aforementioned text by Molecular Mechanics by Burkert et al. (e.g., see pp 39 & 40) For instance, the stretching force constant $k_r$ may be determined by an analysis of a molecule's infrared spectra because the vibration frequencies which give rise to the IR bands are related to the molecule's geometry and force constants. The other constants, i.e., angle bending force constant $k_\theta$ and torsion bending constant $k_w$ etc., are similarly determined experimentally.

Conventional molecular mechanics programs require that the user initially input a trial molecular structure including the types of atoms, position coordinates that define their spatial positions, and the bond connections. These initial structure are usually guessed. Once the computer calculates the necessary internal coordinate bond distances, angles, etc., it then proceeds to calculate the steric energy based upon a summation of the energies found from the equations shown in FIGS. 1-4 or through the use of other equivalent equations. Once the steric energy for the trial molecular structure is found, the program then tries to improve the structure by moving the atoms so that the calculated steric energy of the molecule decreases.

There are a number of prior art techniques for optimizing such atomic movements (e.g., "steepest descent"). In essence, each method involves an iterative, over and over, movement of the atoms around their coordinates to determine the direction of atomic movement which leads to an energy minima. In complex molecular structures, this will generally lead to a local minimum, but not necessarily the best minimum (global). This is especially true when complex molecules are being analyzed which have a great number of regional minima.

Thus, the results depend on both the force-field calculations and, to a great extent, the intuition of the person doing the calculation who chose which starting geometries were used.

In attempting to find all the conformations (and therefore also the lowest energy conformation—the global minimum), computer programs exist in the prior art which systematically step through different values of a dihedral angle in the starting structure. For instance, see Wiberg, K. B. and Boyd, R. H. "Journal of the American Chemical Society", 1972, Vol. 94, at page 8426. While this procedure works for small systems, with increasing complexity it is possible to miss the best structure because the step size is too large or because the initial structures for some angles refines to minima which are not "global minima" even for the particularly selected dihedral angle. The odds of finding the global minimum can be improved by stepping through all combinations of values of several dihedral angles; however, the person using the program must decide which angles to vary and by what steps. Too few angles or steps which are too large rapidly increase the chances of missing the best structure.

As above stated, computer programs are available which carry out aspects of the above recited molecular mechanics analytical steps. Some of those programs are made generally available through "Quantum Chemistry Program Exchange", Indiana University, Chemistry Building 204, Bloomington, Indiana 47401. One such program is MM2 by N. L. Allinger. Another program, i.e. MMP2, a program for general molecular mechanics calculations, is available from Molecular Design Limited, 1122B Street, Hayward, California 94541. As aforestated, however, those programs suffer from the drawback that the user is not aware of whether all of the minima have been discovered in any particular atomic arrangement, and, more particularly, whether the molecular structure which gives the lowest steric energy (and is thus most stable) has been found.

It is, therefore, an object of this invention to provide a method for molecular mechanics calculations which has a high probability of finding all of the steric energy minima for a particular molecular structure.

It is still another object of this invention to provide a molecular mechanics calculation method wherein a high probability is present of finding molecular structures which exhibits the best global steric energy minima.

SUMMARY OF THE INVENTION

The invention disclosed herein is a stochastic ("Monte Carlo") method for determining the likely structure of a molecule by starting with an initial molecular structure along with given atomic coordinate positions and defined bonds between atoms. Each of the atoms initial X, Y and Z coordinates are modified by the combination therewith of random numbers to create a new randomly chosen coordinate position for each atom. A predetermined constraint is placed on the distance of each new coordinate from each initial coordinate. The new structure is optimized using a molecular mechanics program and then the steric energy of the reconfigured molecule is then calculated, stored and a new set of random numbers combined with the atomic coordinates and the steric energy of the new structure calculated. The process is repeated until most, if not all steric minima, are detected and the structures associated therewith are determined.

DETAILED DESCRIPTION OF THE INVENTION

The invention to be presented hereinbelow differs from prior molecular mechanics methods for defining structures at a basic level. As above stated, prior art methods start with a selection of an initial, trial molecular structure and increment the positions of the atoms in a defined and iterative way in order to determine molecular energy minima or conformations. The method of this invention begins with any trial structure and initially refines it to a local minima. Then, a random "kick" is applied to all of the atoms in the molecule. A random number generator is employed to compute an independent, random increment or decrement for each coordinate of each atom. The structure, as thus perturbed, is then re-refined using any of a number of standard molecular mechanics refinement programs. There are two possible results from this procedure. The molecule can return to its initial confirmation, or it can revert to another conformation. All distinct (i.e., minimum energy) conformations previously found are stored so that any newly found one can be compared and recognized either as new or as repetitive of a previously stored structure.

Turning now to FIGS. 5-8, a flow chart illustrating the method of this invention will be hereinafter described. It should be noted that software embodying the method of the invention has been successfully tested and run on a Digital Equipment Corporation Micro-Vax II minicomputer. Obviously, however, the flow charts to be hereinbelow described may be configured in any computer language and run on any appropriate computer.

Figure 5:
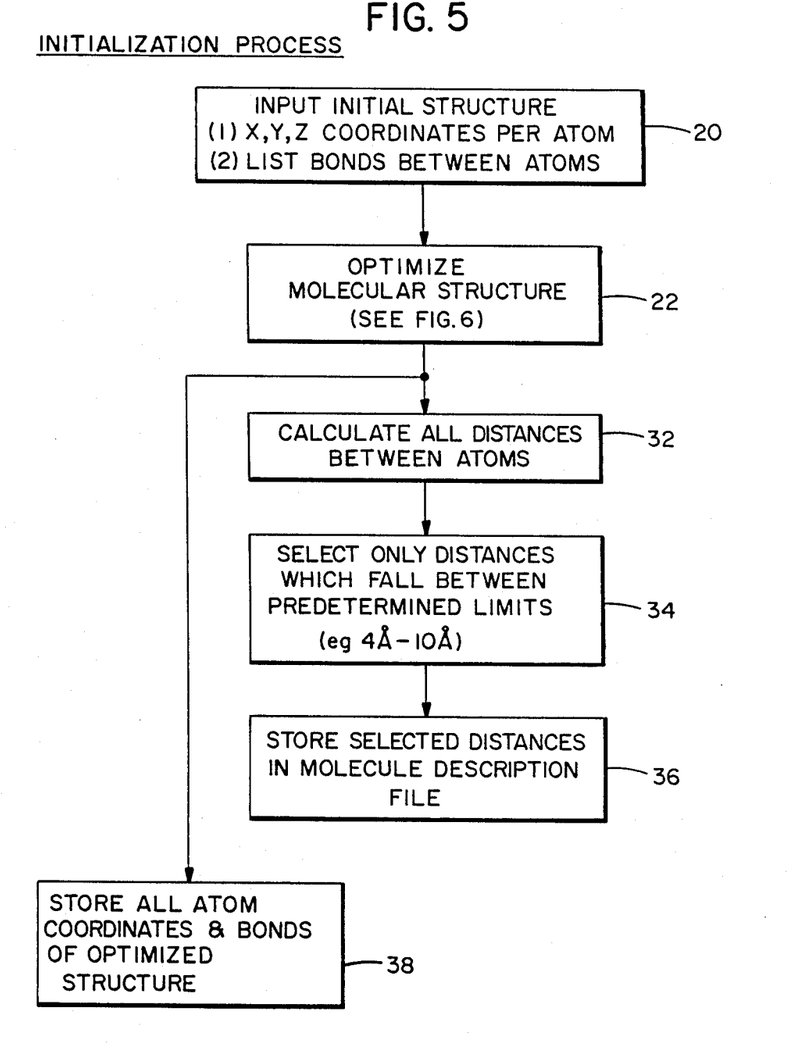
FIG. 5 is a flow diagram of the initialization process of the invention.

In FIG. 5, Box 20 indicates that the method is commenced by inputting the initial structure of a molecule to be investigated. That involves a description of each atom by X, Y and Z coordinate numbers and the definition of all bonds between atoms. The initial molecular structure is then optimized as shown by Box 22. In other words, the atoms' positions are modified until an energy minima is detected. Optimization procedure 22 is shown in detail in FIG. 6.

Initially as indicated by Box 24, the energy functions shown in FIGS. 1-4 are calculated for the starting molecular structure to obtain the structure's steric energy. Since there are no other previously obtained steric energies for comparison, it cannot be known whether the calculated steric energy is a minimum or not. In such a case, decision Box 26 indicates that no energy minima has been found, and the method continues by calculating the derivatives of each energy function with respect to displacement of the atoms in the X, Y and Z directions (as shown at Box 28). The derivative of energy with respect to displacement provides X, Y and Z component forces on each atom. The program then vector sums all such forces on each atom as shown at Box 30. The vector sum indicates the direction of the net force acting on each atom and the program (as shown at Box 32) then increments the atoms' coordinates in that direction by a preset amount. Once each of the atoms is moved, the program repeats by calculating the energy functions and net steric energy for the new structure. This procedure continues with each new molecular structure having its steric energy calculated and compared with previously stored steric energies for previously derived structures. A minimum is detected when the steric energy for a new structure is found to be higher than that obtained for previous structures, in which case the optimization process ceases.

It should be noted, that the optimization portion of this method is not, per se, novel and has been configured in previously available programs for molecular steric energy minimization, e.g. MM2 by Allinger. Any other suitable optimization algorithm may also be used.

Returning now to FIG. 5, the program proceeds as shown at Box 32, to calculate all distances between atoms for the molecular structure found in the optimization process to exhibit a steric energy minima. Since each atom's position is defined by three coordinates (i.e., X, Y and Z), simple geometry is used to determine those distances. Boxes 34 and 36 indicate that the program then selects only certain interatomic distances which fall between predetermined limits and stores them in a "molecular description file". In parallel, as shown by Box 38, all of the atomic coordinates and bonds for the optimized molecular structure are also stored.

The reason for storing the molecular descriptions is to be able to readily compare subsequently found molecular structures with ones already found independent of how or whether they have been rotated, or otherwise translated from previously found molecular structures. By retaining only interatomic distances which fall between preset limits and then comparing those with the same distances subsequently found for newly calculated molecular structures, the comparison problem is greatly reduced. In most instances, interatomic distances between four angstroms and ten angstroms have been found to be useful for subsequent comparisons. The shorter interatomic distances, i.e. less than four angstroms, are generally bonding distances or distances between non-bonded triatomic atoms and do not change much with conformational changes. The maximum distance cutoff is used to limit the size of the data base since, with a large molecule, the number of longer distances can become very large.

To summarize, subsequent to the initialization process, an optimized molecular structure has been found; certain distances between its atoms have been calculated and stored in a molecular description file for subsequent comparison to newly found optimized molecular structures; and the complete description of the molecular optimized structure has been stored.

Figure 7:
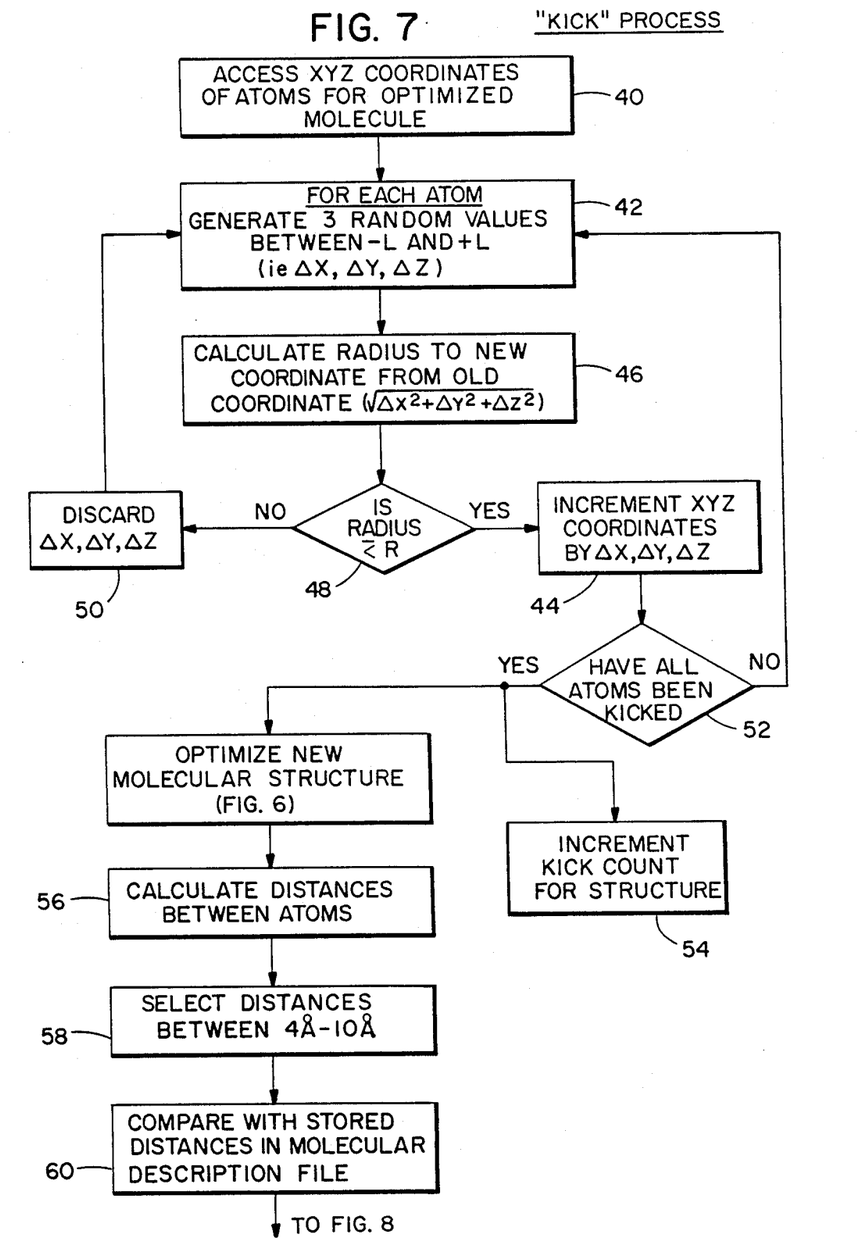
FIGS. 7 and 8 illustrate a flow diagram of the "kick" process and molecule comparison features of the invention.

Referring now to FIG. 7, the "kick" process will be described. As shown at Box 40, the X, Y and Z coordinates previously stored (see Box 38—FIG. 5) for the atoms in the optimized molecule are accessed. A random number generator then provides three random values between $-L$ and $+L$ where L=the maximum radial distance an atom is to a be moved (see Box 42). Subsequently, the radial distance $\sqrt{\Delta X^2 + \Delta Y^2 + \Delta Z^2}$ is calculated as shown in Box 46 to determine if the distance to the new coordinate exceeds the predetermined limit L. If the radial distance does exceed that limit, (see decision Box 48), the random values X, Y and Z are discarded (Box 50) and a new set of random numbers are generated and tested. If however the calculated radial distance is found to be within the prescribed limit, each X, Y and Z coordinate for a chosen atom is then incremented by a random value $\Delta X$, $\Delta Y$, & $\Delta Z$ so that its new coordinates are $X+\Delta X$, $Y+\Delta Y$, and $Z+\Delta Z$ (Box 44). The program continues and repeats the process for all atoms of the structure (decision Box 52).

Essentially, this procedure establishes a sphere of radius L within which each atom's movement is confined. The probability of an atom moving to any point within this sphere is the same. The size of this sphere is empirical and it has been found that limits between 2 and 4 angstroms provide sufficient atomic re-arrangement to assure a high probability of the molecular structure's moving to another conformation. If too small a radius is chosen, too often it happens that the structure falls back to that existing previous to the kick. Larger random kicks increase the probability of conformational transitions. However, if the maximum radius is made too large, the computing time to reach optimization increases and also a greater number of high energy conformations are found (usually undesirable).

Figure 6:
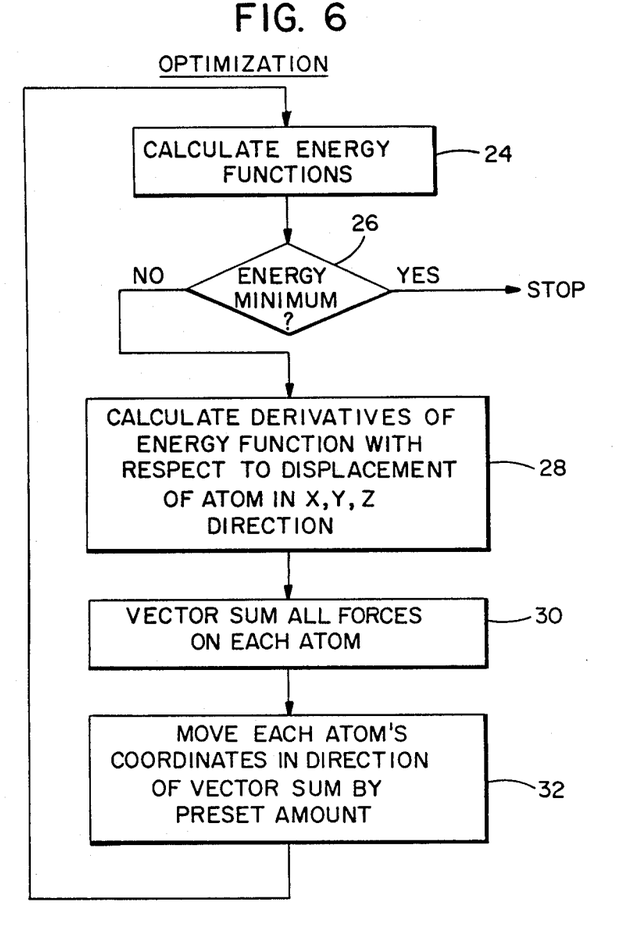
FIG. 6 is a flow diagram of the molecular optimization process employed by the invention.
Figure 8:
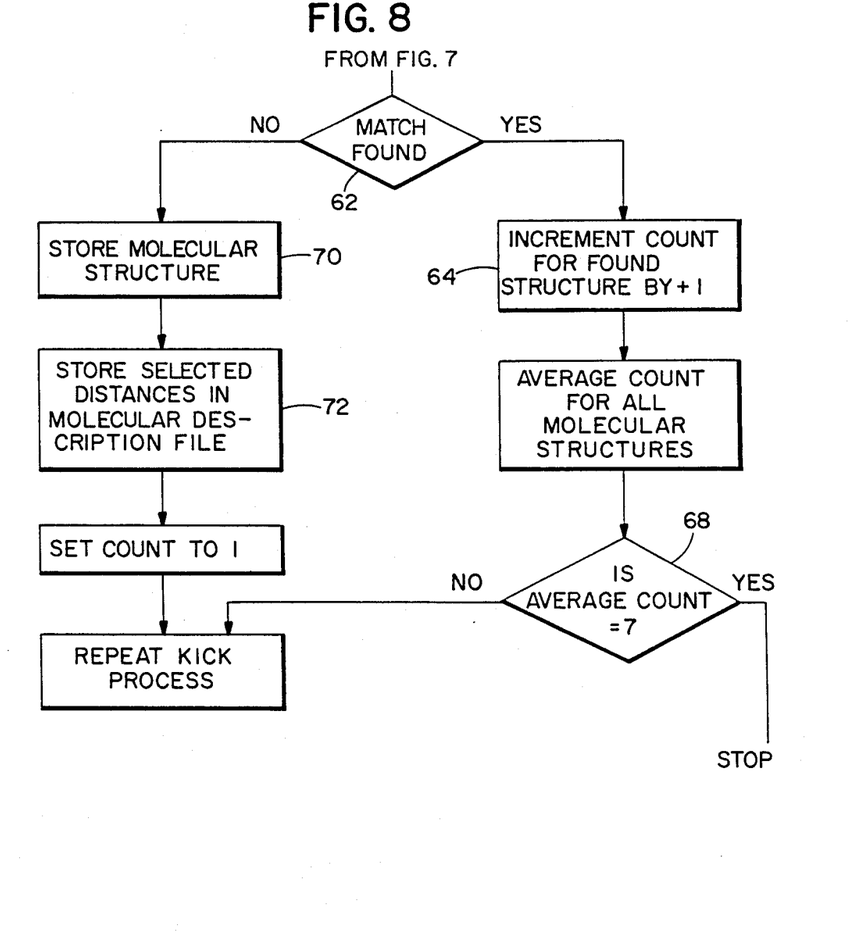

Once all of the atoms of the structure have been randomly "kicked" in the above manner, a kick count for the structure is incremented by an integer amount (Box 54). Then, the new molecular structure is optimized as shown in FIG. 6, the distances between atoms calculated (Box 56), interaomic distances selected (Box 58), and those distances compared with previously stored distances in the molecular description file (Box 60). As shown in FIG. 8, if a match is found (decision Box 62) indicating that the newly optimized molecular structure has a duplicate in the molecular description file, a count associated with that particular molecule is incremented by 1 to indicate the number of times the conformation has been derived via the optimization process (Box 64).

It can be shown statistically that when each structure has been found an average of seven times, there is better than a 99% probability of having found any particular minimal steric energy structure. This assumes that there is an equal chance of finding all structures. Thus, until the average "found" count in the molecular description file equals seven, the process continues (as shown by decision Box 68).

If a new structure finds no match in the molecular description file (decision Box 62), that indicates that a new steric energy minima molecular structure has been found. The atomic coordinates of that structure are stored along with the selected interatomic distances in the molecular description file (boxes 70,72). The "found" count for that structure is set to one, and the kick process is then repeated using the newly found molecular structure as the starting point. The program then continues until no new structures are being found, and all structures is the molecular description file have been found a predetermined average number of times.

It should be understood that it is not absolutely necessary to start from the molecular structure previously found to exhibit a minimum steric energy in the "kick" process. Any molecular structure can serve as a starting point for the kick procedure and under certain circumstances, different structures may be utilized. For instance, to explore a molecular surface in the vicinity of one particular structure, the particular structure may serve as the starting point.

Figure 12:
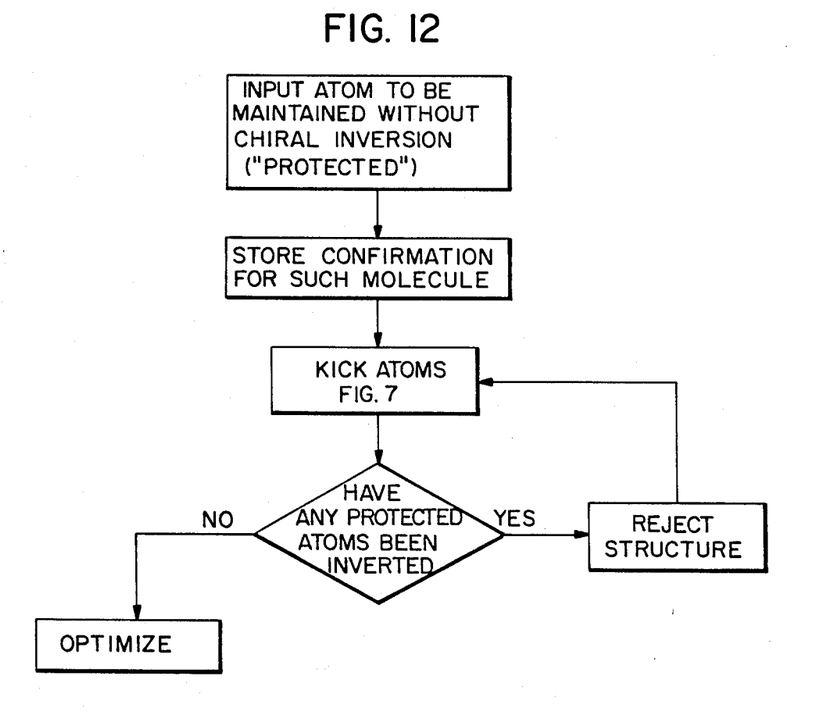
FIG. 12 is a flow diagram of a modification of the method of the invention.

It has been found that a three angstrom kick is big enough to readily invert the chirality of carbons. In such a case, various diasteromeric conformations may be generated in a single run of the method independent of the starting isomer. While that may be useful for certain studies, it is not appropriate for investigating a natural product with many chiral centers since making the search less efficient. In such a case, the method of the invention is modified to control these inversions (See FIG. 12). Thus, atoms to be maintained without inversion are so noted at the time of input and the program remembers the chirality of all atoms so indicated. After every kick, the program checks these atoms to see if any have been inverted (one method would use the Cahn, Prelog and Ingold algorithm which determines whether atoms are in the R or S state of chirality). If any indicated atom has been inverted, the kick is rejected and the previous structure is rekicked until a "legal" structure is found. This preserves the randomness of the method but prevents the program from entering unwanted structural territory. Since the set of structures found is smaller, less time is required for a complete search.

Figure 9:
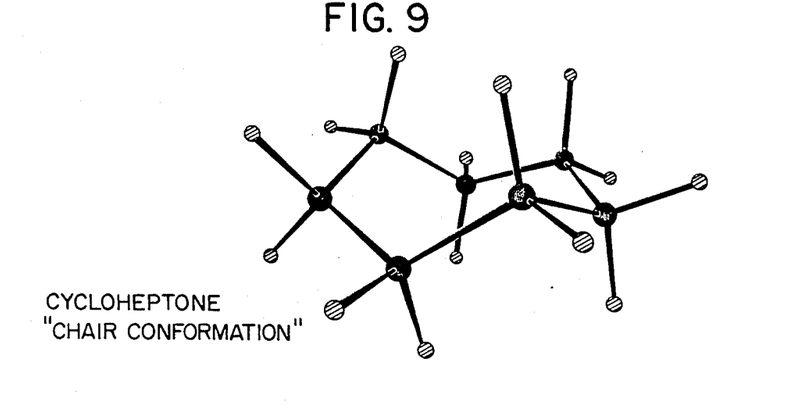
FIG. 9 is a diagram illustrating one form of a cycloheptane molecule.
Figure 10:
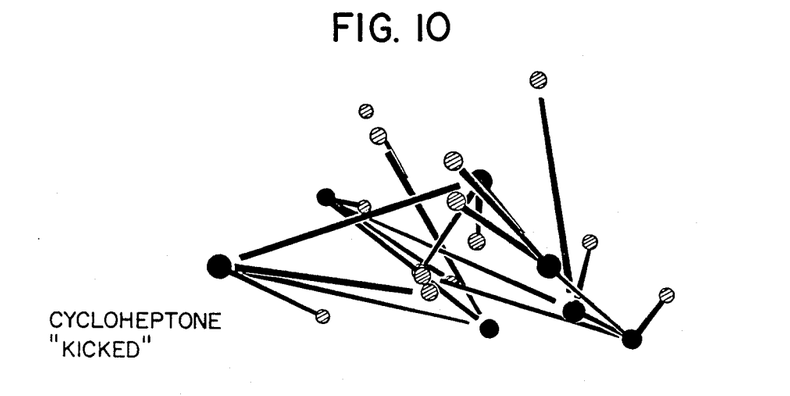
FIG. 10 is a diagram of the cycloheptane molecule after its atoms have been "kicked".
Figure 11:
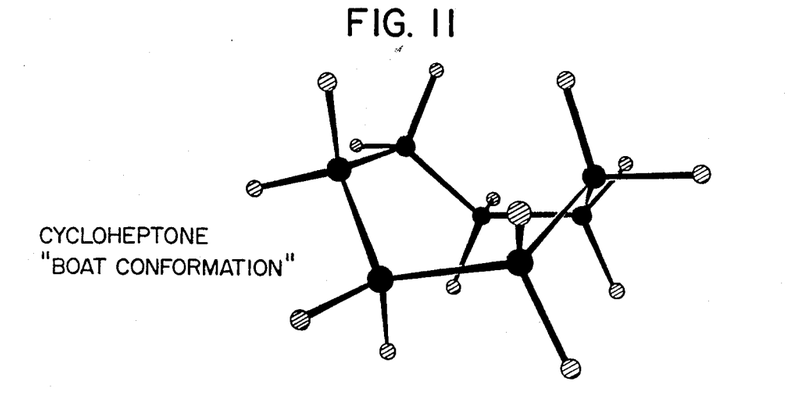
FIG. 11 is a diagram illustrating another form of the cycloheptane molecule after it has been optimized.

Turning now to FIGS. 9, 10 and 11, FIG. 9 is a diagram of a molecule of the hydrocarbon cycloheptane in the "chair" conformation. In such a molecular structure, the cycloheptane molecule exhibits an MM2 steric energy of 14.2 kilocalories. FIG. 10 shows the same cycloheptane molecule after it has been subjected to a "kick" in accordance with the above described procedure. FIG. 11 shows the results of the optimization of the molecular arrangement of FIG. 10, i.e. the cycloheptane molecule has taken a boat conformation and exhibits a 17.46 kilocalory MM2 steric energy.

Appendix A (not printed, but included in the file wrapper) is a source code listing of a program which embodies the invention hereof.

It is to be understood that the above described embodiments of the invention are illustrative only and that modifications throughout may occur to those skilled in the art. Accordingly, this invention is not to be regarded as limited to the embodiments disclosed herein, but is to be limited as defined by the appended claims.

I claim:

1. A method for determining a likely structure of a molecule, the method comprising:
   (a) selecting an initial molecular structure, each of whose atoms is specified by a set of spatial coordinates and wherein bonds between said atoms are specified;
   (b) generating a plurality of random numbers;

(c) combining a random number with each spatial coordinate of each said atom to create a new set of spatial coordinates for each said atom and thus a new molecular structure;

(d) calculating steric energy of said new molecular structure; and (e) repeating steps (a)-(d) until a molecular structure is found which exhibits a steric energy minima.

2. The method of claim 1 including the further steps of:

(f) storing spatial coordinates of the atoms in the molecular structure found in step (e);

(g) storing a selected subset of interatomic distances in said found molecular structure.

3. The method of claim 2, including the further steps of:

(h) repeating steps (a)-(e) beginning with a last found molecular structure until another molecular structure exhibiting a steric energy minima is found;

(i) comparing a selected subset of interatomic distances in the molecular structure found in step (h) with selected subsets of interatomic distances previously stored, to determine if there is or is not a match between said previously stored interatomic distance subsets and said subset for the molecular structure found in step (h).

4. The method of claim 3 further including the steps of:

(j) storing the atomic coordinates of the molecular structure found in step (h) if a match is not found in step (i); or (k) discarding the atomic coordinates of the molecular structure found in step (h) if a match is found in step (i); and (l) storing a count of a number of times the molecular structure found in step (h) has been found.

5. The method of claim 4 further including the step of:

(m) terminating the method of steps (a)-(l) when an average count for the molecular structures determined by step (l), reaches a predetermined count.

6. The method of claim 1 further including the steps of:

(f) determining whether a radial distance between a new set of spatial coordinates for each atom created in step (c) and the spatial coordinates to which the random numbers were added is greater than a predetermined maximum; and (g) repeating steps (b) and (c) until said radial distance is not greater than said predetermined maximum.

7. The method of claim 6 wherein said radial distance is not less than two nor more than four angstroms.

8. The method of claim 6 further including the steps of:

(h) storing the coordinates of the atoms in said found molecular structure;

(i) storing a selected subset of interatomic distances in said found molecular structure;

(j) repeating steps (a)-(e) for a different initial molecular structure until a molecular structure exhibiting a steric energy minima is again found;

(k) comparing a selected subset of interatomic distances in the molecular structure found in step (j) with selected subsets of interatomic distances previously stored, to determine if there is or is not a match between said previously stored interatomic distance subsets and said subset for the molecular structure found in step (j).

(l) storing the atomic coordinates of the molecular structure found in step (j) if a match is not found in step (k); or (m) discarding the atomic coordinates of the molecular structure found in step (j) if a match is found in step (k); and (n) indicating a count for a number of times the molecular structure found in step (j) has been found.

9. The method of claim 1 including the further steps of:

(f) indicating that the chirality of selected atoms in said initial molecular structure is not to be inverted;

(g) rejecting any new molecular structure resulting from step (c) if any of said selected atoms have been inverted in said new molecular structure; and (h) repeating steps (b) and (c) until a new molecular structure results wherein all said selected atoms remain non-inverted, at which time step (d) is performed.

* * * * *

UNITED STATES PATENT AND TRADEMARK OFFICE
CERTIFICATE OF CORRECTION

PATENT NO. : 4,855,931
DATED : August 8, 1989
INVENTOR(S) : Martin Saunders

It is certified that error appears in the above-identified patent and that said Letters Patent is hereby corrected as shown below:

Col. 1, before "BACKGROUND OF THE INVENTION" insert:

--This invention was made with Government support under grant number CHE 8310857 awarded by the National Science Foundation. The Government has certain rights in the invention.--

Signed and Sealed this

Seventeenth Day of July, 1990

Attest:

HARRY F. MANBECK, JR.

Attesting Officer

Commissioner of Patents and Trademarks